United States Patent [19]

Ueno et al.

[11] 4,202,969
[45] May 13, 1980

[54] METHOD OF PRODUCING NITROGEN-CONTAINING POLYSACCHARIDES

[75] Inventors: Saburo Ueno, Ichigayadai; Chikao Yoshikumi, Kunitachi; Fumio Hirose, Tokyo; Yoshio Omura, Tanashi; Toshihiko Wada, Mibu; Takayoshi Fujii, Tokyo; Eiichi Takahashi, Kawaguchi, all of Japan

[73] Assignee: Kureha Kagaku Kogyo Kabushiki Kaisha, Tokyo, Japan

[21] Appl. No.: 788,992

[22] Filed: Apr. 19, 1977

[30] Foreign Application Priority Data

Jul. 7, 1976 [JP] Japan .................. 51-80664

[51] Int. Cl.² .............................. C07H 1/08
[52] U.S. Cl. ............................. 536/1; 424/181; 536/18
[58] Field of Search ........................... 536/1

[56] References Cited

U.S. PATENT DOCUMENTS

| | | | |
|---|---|---|---|
| 3,436,311 | 4/1969 | Ferguson et al. | 536/1 |
| 3,436,346 | 4/1969 | Westover et al. | 536/1 |
| 3,759,896 | 9/1973 | Komatsu et al. | 536/1 |
| 3,822,250 | 7/1974 | Kimura et al. | 536/1 |
| 3,933,788 | 1/1976 | Kang et al. | 536/1 |
| 4,051,314 | 9/1977 | Ohtsuka et al. | 536/1 |

FOREIGN PATENT DOCUMENTS 1331513  9/1973  United Kingdom ............ 536/1

*Primary Examiner*—Johnnie R. Brown
*Attorney, Agent, or Firm*—Stevens, Davis, Miller & Mosher

[57] ABSTRACT

The fungi belonging to the Coriolus genus are extracted by using a dilute alkaline solution having a concentration within a certain specified range whereby the low molecular weight substances with molecular weight of less than 5,000 are obtained in there extract solution. These low molecular weight substances are separated from the extract solution to obtain a nitrogen-containing polysaccharide having excellent anti-tumor activity.

3 Claims, No Drawings

000

METHOD OF PRODUCING NITROGEN-CONTAINING POLYSACCHARIDES

FIELD OF THE INVENTION

This invention relates to a method of producing nitrogen-containing polysaccharides having an anti-tumour activity and other excellent pharmacodynamic properties from a fungus of the class Basidiomycetes belonging to the Coriolus genus.

BACKGROUND OF THE INVENTION

It is known that a polysaccharide having an anti-tumour effect can be produced by refining the extract of the Basidiomycetes with an aqueous solvent. This known method, however, has a serious defect that extraction efficiency of the active components is low and hence practical adaptability of this method to industrial production of the anti-tumour substances is poor. This method employs salting-out by use of ammonium sulfate, dialysis, precipitation by use of an organic solvent, or gel filtration as the extract refining means, but such refining means are extremely poor in workability, and hence such method is not of a type advantageous for removing the low molecular weight substances (with molecular weight of less than 5,000) contained in the extract. The low molecular weight substances have almost nil inhibitory activity against Sarcoma-180 solid tumours in mice in intra-peritoneal administration, and further, they have bitterness and a disagreeable odor, so that presence of such substances is undesirable in utilization of the polysaccharides as medicaments.

BRIEF SUMMARY OF THE INVENTION

We have found that a nitrogen-containing polysaccharide having an anti-tumour effect and other various pharmacodynamic effects can be obtained in a high yield when a fungus belonging to genus Coriolus of family Polyporaceae of the class Basidiomycetes is extracted with an aqueous solution having an alkali concentration within a specified range and the obtained extract is refined by means of ultrafiltration and/or reverse osmosis.

The primary object of this invention, therefore, is to provide a method of advantageously producing a nitrogen-containing polysaccharide having an excellent anti-tumour activity and other various pharmacodynamic effects from a fungus belonging to the Coriolus of the Basidiomycetes. The other objects of this invention will become apparent from reviewing the following detailed description of the invention.

DETAILED DESCRIPTION OF THE INVENTION

The "fungus belonging to the Coriolus genus" used as starting material in this invention is a known species of fungi belonging to Polyporaceae of the class Basidiomycetes, such species include, for example, *Coriolus versicolor* (Fr.) Quel., *Coriolus hirsutus* (Fr.) Quel., *Coriolus consors* (Berk.) Imaz., *Coriolus conchifer* (Schw.) Pat., *Coriolus pubescens* (Fr.) Quel., *Coriolus pargamenus* (Fr.) Pat., and *Coriolus biformis* (Klotz.) Pat. (See COLOURED ILLUSTRATIONS OF FUNGI OF JAPAN by Rokuya Imazeki and Tsuguo Hongo, Vol. I 1974, and Vol. II, 1975). *Coriolus versicolor* (Fr.) Quel.; *Coriolus consors* (Berk.) Imaz.; *Coriolus hirsutus* (Fr.) Quel. and *Coriolus pargamenus* (Fr.) Pat. are deposited on Dec. 25, 1973 under FERM-P No. 2414; on June 24, 1971, under FERM-P No. 988; on Sept. 6, 1974 under FERM-P No. 2711; and on Sept. 6, 1974 under FERM-P No. 2712, respectively, in Fermentation Research Institute, Agency of Industrial Science and Technology (Chiba-shi, Japan), a government organ designated by the Director-General of the Patent Office of Japan. The term "fungus belonging to the Coriolus genus" used in this invention refers to the fruit body and/or mycelium of the fungus, most preferred for use in this invention is the mycelium obtained from artificial culture of *Coriolus versicolor* (Fr.) Quel.

The method of this invention features the steps of extracting the above-mentioned fungus by using a 0.01 N to 2 N aqueous alkaline solution and subjecting the obtained extract to ultrafiltration and/or reverse osmosis to remove low molecular weight components with molecular weight of less than 5,000 from the extract.

The concentration of the alkaline solution used for extraction of the Basidiomycetes in this invention must be within the range of 0.01 N to 2 N because if the such concentration is less than 0.01 N, the result is not much different from that obtained from extraction with water, while if the concentration exceeds 2 N, the result may be decomposition. Preferred extraction of the Basidiomycetes can be satisfactorily accomplished by using an alkaline solution of the above-mentioned concentration range at a temperature of 50° to 100° C., preferably 80° to 98° C., for a period of 20 to 600 minutes. It should be noted that an extraction temperature of lower than 50° C. results in insufficient extraction of the active component, while an extraction temperature of over 100° C. may invite reduction of activity of the obtained active component. The preferred range for extraction time varies depending on the concentration and temperature of the alkaline solution used, but usually it is preferable to use an extraction time within the above-defined range, that is, 20 to 600 minutes. It is possible to obtain a satisfactory result by one extraction, but if desired, extraction may be repeated several times.

Various kinds of alkaline materials, such as sodium hydroxide, potassium hydroxide, ammonia or calcium hydroxide etc., may be used for the alkaline solution in this invention. The use of sodium hydroxide and potassium hydroxide is preferred.

The liquid extract obtained in the above-described procedure is neutralized according to an ordinary method by using a mineral acid such as dilute hydrochloric acid and then subjected to ultrafiltration or reverse osmosis to remove the low molecular weight substances (with molecular weight of less than 5,000) in the extract. It has been common practice to refine the extract by means of salting-out with ammonium sulfate, dialysis, precipitation by use of an organic solvent or gel filtration as mentioned before, but such refining methods were extremely poor in workability, and hence a solution to this problem has been a desideratum. We have studied the significance of each of such refining methods in conjunction with the pharmacodynamic effects of refined product, and found that the solution to this problem resided in elimination of the low molecular weight substances contained in the extract. And as a result of further study for a more rational and workable method for removal of such low molecular weight substances, we succeeded in establishing a most effective method of removing the low molecular weight substances with molecular weight of less than 5,000 by adapting the techniques of ultrafiltration and/or reverse osmosis.

The prominent feature of the refining means used in this invention is that the component substances are fractionated according to molecular weight by using a membrane, which may be called a kind of molecular sieves, under pressure. In such fractionating by the membrane, the values of the molecular weights are usually determined according to the kinds of the membrane used, but as fractionating performance depends greatly on the molecular weight and configuration of molecules in the solution, the fractionated molecular weight values indicated in the catalog of the commerical membrane maker and the generally employable environmental conditions are not always applicable to refining of the extract according to this invention. In this respect, it was confirmed that a membrane bearing indication of 5,000 to 15,000 fractionated molecular weights and having 98 to 100% inhibition against cytochrome c (molecular weight 13,000) as standard material is suitable for use in this invention. As for the operating conditions for refining method according to the present invention using the above-mentioned membrane, such conditions matter-of-factly fluctuate to a certain extent depending on the size and shape of the apparatus, throughput of the extract and other factors, but in the case of ultrafiltration, such operation is carried out usually under a pressure of 0.5 to 5 kg/cm$^2$, preferably 1 to 4 kg/cm$^2$, and at a temperature of usually 5° to 70° C. though the operation temperature may vary depending on the type of membrane. In the case of reverse osmosis, the pressure used is usually within the range of 20 to 35 kg/cm$^2$, preferably 20 to 25 kg/cm$^2$, and the temperature is usually within the range of 5° to 20° C.

Generally, it is considered that ultrafiltration is suited for fractionating of material with molecular weights of over 10,000 while reverse osmosis is suited for fractionating of material with molecular weight of less than 1,000. Fractionation for a cut-off point a molecular weight of 5,000, which is intended in this invention, is intermediate to the ranges recommended for the above-mentioned two respective methods, but it was revealed that both methods can be applied to fractionate material with molecular weight of less than 5,000 through suitable selection of the membrane. Therefore, in refining the extract according to the method of this invention, the ultrafiltration and reverse osmosis methods may be used either singly or in combination, and such selection is made by taking into consideration workability and operating eficiency. The fractions with molecular weights of less than 5,000, removed from the liquid extract, are almost nil in inhibitory effect against Sarcoma-180 solid tumours in mice in intra-peritoneal administration, and they also have bitterness and a disagreeable odor, so that it is considered that the presence of such low molecular weight substances is not in the least beneficial but rather detrimental to the pharmacodynamic effect of the final product of this invention, a nitrogen-containing polysaccharide.

The extract from which the low molecular weight substances (with molecular weight of less than 5,000) have been removed by the above-mentioned refining operation is subjected to spray-drying or freeze-drying and then prepared into commercial products.

The substance obtained in the above-described manner according to this invention is liver brown in color and has a nitrogen content of from 2 to 8%, in many cases 3 to 6%. It exhibits no distinct melting point and is gradually blackened and decomposed at a temperature of higher than about 120° C. As for solubility of the substance of this invention, it is soluble in water but almost insoluble in alcohol, pyridine, chloroform, benzene and hexane. It is also tasteless and odorless.

Various color reaction tests on the substance obtained according to the method of this invention gave the results as shown in Table 1 below.

Table 1

| | (Color reaction tests) | |
|---|---|---|
| | Color | Results |
| α-naphthol sulfuric acid reaction (Molish's reaction) | Purple | Saccharides Confirmed |
| Indole sulfuric acid reaction (Disch's reaction) | Brown | Saccharides Confirmed |
| Anthrone sulfuric acid reaction | Greenish blue | Saccharides Confirmed |
| Phenol sulfuric acid reaction | Brown | Saccharides Confirmed |
| Tryptophane sulfuric acid reaction | Purplish brown | Saccharides Confirmed |
| Lowry-Folin process | Blue | Peptide bonds Confirmed |
| Ninhydrin reaction after hydrochloric acid hydrolysis | Greenish blue | α-amino acids Confirmed |

The results shown in the above table imply that the substance of this invention (hereinafter referred to as the present substance) is a nitrogen-containing polysaccharide. The molecular weight of the present substance, as measured according to an ultra-centrifugal method, ranged from 5,000 to 300,000 and the weight-average molecular weight ranged from 10,000 to 100,000. Other measuring methods, such as fractionating by use of an ultrafiltration membrane, also gave the values of 10,000 to 100,000. Therefore, it may be estimated, with high reliability, that the average molecular weight of the present substance is within the range of 10,000 to 100,000.

The nitrogen-containing polysaccharide obtained according to the present invention not only demonstrated a high anti-tumour activity with high inhibition ratio against Sarcoma-180 solid cancer in mice in intra-peritoneal administration but also proved effective in oral administration. This is indicative of very high availability of the nitrogen-containing polysaccharide of this invention as an oral anti-tumour agent, and in fact, such effect has been confirmed in various experiments. Oral administration of the present substance also produced an excellent effect in improvement of liver function, increase of appetite, adjustment of intestinal disorders and promotion of urination. It is also effective for treatment of leprosy.

As described above, it is possible according to the present invention to obtain a nitrogen-containing polysaccharide which demonstrates an excellent anti-tumour activity as well as other pharmacodynamic effects such as above-mentioned not only in intra-peritoneal administration but also in oral administration, by a relatively simple technique and in a high yield as mentioned in the following embodiments.

EXAMPLE 1

200 gr of dry mycelia of *Coriolus versicolor* (Fr.) Quel. (FERM-P No. 2414) (moisture content: 8.8%, gross nitrogen content: 2.5%) was added in 4 liters of 0.1 N NaOH solution and extracted under agitation in a boiling water bath at internal temperature of 90° to 95° C. for one hour, and then the mixture was cooled to a temperature of below 50° C. and gradually admixed with 1 N HCL solution to adjust pH to 7.0. Then the solids were removed by suction filtration and these solids were washed with 500 cc of water to obtain 4.2 liters of liquid extract in all. This liquid extract was then subjected to ultrafiltration, by using a desk-top ultrafilter by Amicon Inc. (ultrafiltration membrane: PM-5), under agitation and cooling with an operating pressure of 1.5 kg/cm$^2$ at 10° C. to remove low molecular weight substances with molecular weights of less than 5,000, followed by concentration to obtain 300 cc of processed solution. This solution was further subjected to freeze-drying to obtain about 26.6 gr of a liver brown powder (yield: 13.5%). This powder had a moisture content of 7.5% and elemental analysis thereof gave the following composition: C: 40.5%; H: 6.2%; N: 5.8%; O: 47.5%. (The percent of oxygen is the value obtained by subtracting the total percent of other elements from 100). It was easily soluble in water. Also, it showed as high as 90% inhibition ratio against Sarcoma-180 solid tumour in mice in intraperitoneal administration and 65% inhibition ratio in oral administration.

The anti-tumour effect of the products according to this invention was determined according to an ordinary method which is briefly described below.

Sarcoma-180 tumour cells were transplanted in the abdominal cavities of mice, and after allowing growth of the cells for a period of 7 days, 10$^6$ of these cells were further transplanted under the skin of the axilla of other mice to form solid tumours. Administration of the product to be tested was started from 24th hour after transplantation. In the case of intra-peritoneal administration, the product was administered in a dose of 10 mg/kg per administration once every other day for 20 days for a total dosage of 0.2 ml per 20 gr of mouse body weight, and in the case of oral administration, the product was administered in a dose of 1000 mg/kg per administration once a day for 20 days for a total dosage of 0.2 ml per 20 gr of mouse body weight. The tumours were enucleated on the 25th day after transplantation, and the tumour growth inhibition ratio was calculated from the average tumour weight in the mice to which the product of this invention was administred and the average tumour weight in the control mice. For the sake of comparison, the extraction and refining treatment was performed under the same conditions but by using water instead of 4 liters of 0.1 N NaOH solution. The product yield was 7.8%, or about 60% of that attained with the method of this invention.

EXAMPLE 2

500 gr of living mycelia of *Coriolus versicolor* (Fr.) Quél. (FERM-P No. 2414) (moisture content: 70.8%; gross nitrogen content: 2.6% calculated on the dry base) mixed in 2 liters of water and ground by a juice mixer for 10 to 20 minutes, and the mixture was then gradually admixed with 500 cc of 1 N-NaOH solution and extracted in a hot water bath at 90° to 95° C. for 2 hours, followed by neutralization with HCl, washing and separation of cells according to the procedure of Example 1. The obtained extract was subjected to ultrafiltration by using a desk-top ultrafilter (ultrafiltration membrane: G-05T membrane by Bio-Engineering Co.) to eliminate the low molecular weight substances of a molecular weight of less than 5,000, followed by concentration and freeze-drying to obtain 24.2 gr of liver brown powder (yield: 15.1%). This powder was 7.6% in moisture content and 6.0% in gross nitrogen content and had insoluble portion of approximately 20% when dissolved in water. The remaining portion was easily soluble in water. (Elemental analysis showed C: 41.2%; H: 6.1%; N: 6.0%; O: 46.7% (percent of oxygen being the value obtained by subtracting the total of C, H and N values from 100)). This powder was dissolved and, after removing the insolubles by a filter paper (No. 5c), its inhibitory action against Sarcoma-180 solid tumour in mice was examined. It showed as high as 93% inhibition ratio in the case of intra-peritoneal administration and 70% inhibition ratio in the case of oral administration.

EXAMPLE 3

2 kg of dry cells of *Coriolus versicolor* (Fr.) Quél. (FERM-P No. 2414) (moisture content: 8.0%, gross nitrogen content: 2.5%) were placed in 20 liters of 0.4 N NaOH solution and subjected to 2-hour extraction under agitation in an extraction vessel equipped with a heating-cooling jacket and an agitator while regulating the jacket temperature so that the internal temperature stayed at 90° to 95° C. The extracted slurry was cooled down to room temperature and, after adjusting pH to 7.0 by adding 2 N-HCl portionwise with agitation, the residue (solids) was separated from the liquid extract by a centrifugal separator. The residue (solids) was mixed with 20 liters of 0.4 N-NaOH solution and subjected to a similar extraction treatment at 90° to 95° C. for 2 hours, followed by cooling, neutralization and centrifugal separation (separation of cells) to obtain liquid extract and the residue. The latter was once again subjected to a similar extraction treatment with 0.4 N-NaOH solution for one hour to obtain an extract. This three-times repeated extraction operation gave about 58 liters of liquid extract in total. This liquid extract was concentrated to approximately 10 liters by a vacuum concentrator and then treated in an ultrafilter (using HFA-180 Membrane by Abcor Inc.) at 10° C. and under 30 psi to remove the low molecular weight substances (with molecular weight of less than 5,000), followed by additional concentration to obtain approximately 5 liters of processed solution. Then, about 70 liters of the solution containing the low molecular weight fraction discharged from the ultrafilter was subjected to a reverse osmoser (using AS-205 membrane by Abcor Inc.) to remove the low molecular weight substances and then concentrated to obtain approximately 5 liters of processed solution. The operating conditions used for this treatment were as follows: average pressure: 25–30 kg/cm$^2$; treating temperature: about 10° C. Then the solutions obtained from the ultrafiltration and reverse osmotic treatments were put together and the 10 liters of the combined solution spray dried to obtain about 395 gr of liver brown powder (yield: 19.9%). This powder had a moisture content of 7.0% and its elemental analysis gave the following results: C: 40.8%, H: 6.0%, N: 4.0%; O: 49.2%. The inhibition ratio of this product against Sarcoma-180 solid tumour in mice was 92% in the case of intra-peritoneal administration and 70% in the case of oral administration. It was easily soluble in water.

What is claimed is:

1. A method of producing a nitrogen-containing polysaccharide which comprises:

(a) extracting *Coriolus versicolor* (Fr.) Quél. with an aqueous alkaline solution having a concentration within the range of from 0.01 to 2.0 N at a temperature of from 50° to 100° C.;

(b) neutralizing the resultant extract and including an alkaline salt therewith at a concentration of at least 0.4 M/l, whereby the molecular shape of said polysaccharide is rendered more spherical; and (c) subjecting the thus-spherically modified polysaccharide to ultrafiltration through a membrane as a molecular seive under a pressure of at least 0.5 kg/cm$^2$, whereby portions of the mixture having a molecular weight of less than 5000 are removed therefrom.

2. A method according to claim 1, wherein said aqueous alkaline solution is a sodium hydroxide solution.

3. The method of claim 1, wherein said temperature is 80° to 98° C.